United States Patent [19]

Aoyagi et al.

[11] Patent Number: 4,642,307
[45] Date of Patent: Feb. 10, 1987

[54] 1-PHENOXY-3-(4-PHENYLPIPERIDINO)-2-PROPAND HAVING BOTH ALPHA- AND BETA-ADRENERGIC ACTION

[75] Inventors: Yoshiaki Aoyagi; Takashi Okubo; Toshio Tomita; Hiroshi Nishida; Hiroshi Enomoto, all of Kyoto, Japan

[73] Assignee: Nippon Shinyaku Co., Ltd., Japan

[21] Appl. No.: 476,857

[22] Filed: Mar. 18, 1983

[51] Int. Cl.$^4$ .................. A61K 31/495; C07D 401/00
[52] U.S. Cl. .................................. 514/252; 514/212; 514/227; 514/233; 540/524; 540/578; 544/121; 544/360; 544/372
[58] Field of Search ............... 544/360, 372; 424/250; 260/243.3; 514/212, 252

[56] References Cited

U.S. PATENT DOCUMENTS 4,413,006 11/1983 Kanno et al. .................. 544/372

FOREIGN PATENT DOCUMENTS 89634 9/1983 European Pat. Off. .
2834114 2/1980 Netherlands .

OTHER PUBLICATIONS

Franke et al, Chem. Abst. 97=216231b.
Aoyaji et al, Chem. Abst. 100=51240u.
Seidelmann, Chem. Abst. 92=215464q.
Thieme et al, Chem. Abst. 95=169204s.
Schacht et al, Chem. Abst. 83=163806v.

Primary Examiner—Donald G. Daus
Assistant Examiner—Cecilia Shen
Attorney, Agent, or Firm—Jacobs & Jacobs

[57] ABSTRACT 1-phenoxy-3-(4-phenylpiperazino)-2-propanol derivatives of the formula (I):

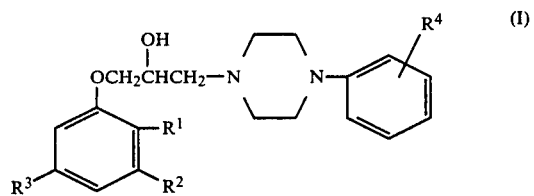

and pharmaceutically acceptable salts thereof wherein $R^1$ is hydrogen, halo or lower alkyl; $R^2$ is pyrrolidino, piperidino, morpholino or perhydroazepino unsubstituted or substituted by carbonyl at the alpha-position; $R^3$ is hydrogen, lower alkyl or lower alkoxycarbonyl; and $R^4$ is hydrogen, lower alkyl unsubstituted or alpha-substituted by lower alkoxy, lower alkoxy, halo or lower alkanoyl are useful for their alpha and beta-adrenergic blocking action and their hypotensive activity in humans and animals.

15 Claims, No Drawings

1-PHENOXY-3-(4-PHENYLPIPERIDINO)-2-PROPAND HAVING BOTH ALPHA- AND BETA-ADRENERGIC ACTION

The present invention relates to novel 1-phenoxy-3-(4-phenyl-piperazino)-2-propanol derivatives of the formula (I):

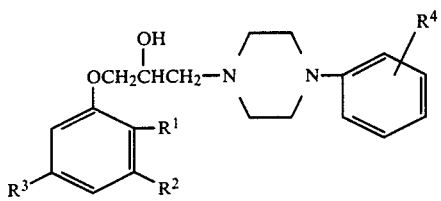

and salts thereof, particularly pharmaceutically acceptable salts thereof, wherein $R^1$ is hydrogen, halo or lower alkyl; $R^2$ is pyrrolidino, piperidino, morpholino or perhydroazepino unsubstituted or substituted by carbonyl at the alpha-position; $R^3$ is hydrogen, lower alkyl or lower alkoxycarbonyl; and $R^4$ is hydrogen, lower alkyl unsubstituted or alpha-substituted by lower alkoxy, lower alkoxy, halo or lower alkanoyl. The compounds and pharmaceutically acceptable salts thereof are useful for their alpha-adrenergic blocking action, their beta-adrenergic blocking action and for their hypotensive activity in humans and animals.

It is known in the art that 1-phenoxy-3-(4-phenyl-piperazino)-2-propanol derivatives exhibit alpha-adrenergic blocking action (see Japanese Patent Application Nos. Sho-55-50950, 56-49360, 56-49361, 56-152420, 56-154431, 56-97227, 56-138174).

It has now been discovered that the novel compounds of formula (I) and their pharmaceutically acceptable salts in which a nitrogen-containing heterocyclic ring having a specific substituent is present at the 3-position of the phenoxy group exhibit alpha-adrenergic blocking action, beta-adrenergic blocking action and are useful for treating hypertension in humans and animals.

It is known in the art that alpha-adrenergic blocking agents may be used in the treatment or prevention of hypertension and for the treatment of peripheral circulation insufficiencies, such as Raynaud's Disease. When such alpha-adrenergic blocking agents are administered as the sole therapeutic agent, the blood pressure of the human or animal receiving the agent is lowered due to the vasodilating action, but in some cases, a reflex tachycardia is simultaneously induced. It is of course possible to prevent reflex tachycardia due to the blood pressure lowering effect of such agents by the simultaneous administration of beta-adrenergic blocking agents. However, according to that procedure, two types of drugs must be administered and the administration can be troublesome.

The compounds of the formula (I) and their pharmaceutically acceptable salts are therefore unique as they are both alpha and beta-adrenergic blocking agents and thus exhibit both strong alpha-adrenergic blocking action and strong beta-adrenergic blocking action. The compounds of the formula (I) and their pharmaceutically acceptable salts are neither "prazosin which possess strong alpha-adrenergic blocking action but do not possess beta-adrenertic blocking action" nor "labetalol which possess comparatively strong beta-adrenergic blocking action but which exhibit weak alpha-adrenergic blocking action". The compounds of formula (I) and said salts exhibit a vasodilating action due to their strong alpha-adrenergic action and exhibit an excellent effect on the heart rate resulting from the hypotensive activity due to their beta-adrenergic blocking action. In addition, the compounds of the present invention do not exhibit anti-diuretic effects which are often observed following administration of other adrenergic blocking agents. The toxicity of the compounds of the present invention and their pharmaceutically acceptable salts is low.

According to one embodiment of the present invention, $R^1$ is hydrogen, fluoro, chloro, bromo or alkyl of 1 to 4 carbon atoms.

According to a further embodiment of the present invention, $R^3$ is hydrogen, alkyl of 1 to 4 carbon atoms or alkoxycarbonyl of 1 to 4 carbon atoms in the alkoxy moiety.

According to a further embodiment of the present invention, $R^4$ is hydrogen, alkyl of 1 to 4 carbon atoms unsubstituted or substituted by alkoxy of 1 to 4 carbon atoms, alkoxy of 1 to 4 carbon atoms, fluoro, chloro, bromo or alkanoyl of 1 to 4 carbon atoms in the alkyl portion.

Hypertension derives from various causes. It results in many diseases and may add to the severity of various conditions such as cerabrovascular disturbances (such as cerabral hemorrhage, cerabral infarction, cerebral arteriosclerosis and the like), ishemic heart diseases (such as mycocardial infarction, angina pectoris and the like), congestive heart failure and renal failure. In order to prevent such complications and to inhibit the worsening of such conditions, it is very important therapeutically that high blood pressure be lowered to a more normal level.

The compounds of the formula (I) and their pharmaceutically acceptable salts exhibit a strong blood pressure lowering action.

The compounds of the present invention may be produced by various routes. One representative route is as follows:

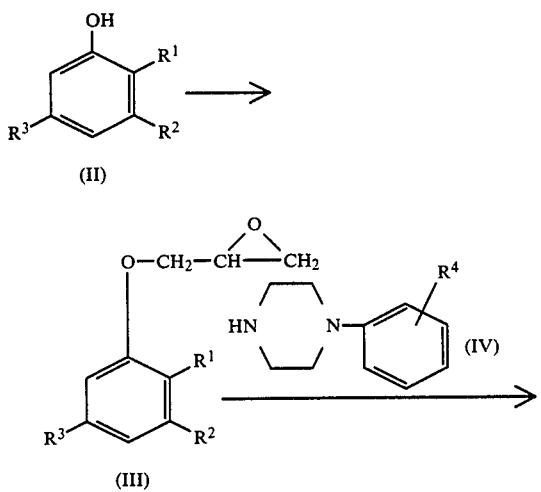

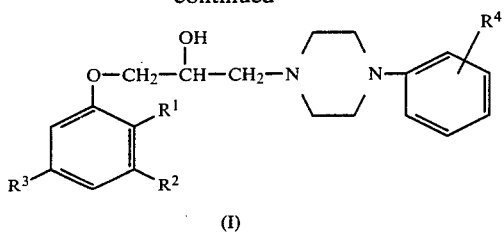

(I)

wherein $R^1$, $R^2$, $R^3$ and $R^4$ are as above defined.

Thus, the phenolic compound of the formula (II) is reacted with epihalogenohydrin in a suitable solvent in the presence of a suitable carbonate such as potassium carbonate to give the corresponding epoxy compound (III). Then the epoxy compound (III) is reacted with an amine of the formula (IV) in a suitable solvent to produce compounds of the formula (I). The term "suitable solvent" used hereinabove refers to a solvent which dissolves the starting materials even to a slight extent and which will not react with the other reactants.

The compounds of the formula (I) and their pharmaceutically acceptable salts may be formulated into pharmaceutical compositions by combining a therapeutically effective amount of a compound of the formula (I) or a pharmaceutically acceptable salt thereof and a pharmaceutically acceptable carrier. Suitable pharmaceutical compositions according to the present invention may contain from 0.1% to 99.5% of a compound of the formula (I) or a pharmaceutically acceptable salt thereof or more preferably from about 1% to about 80%. Such pharmaceutical compositions are preferably in dosage unit form; i.e., physically discrete units containing a predetermined amount of the compound of the formula (I) or a pharmaceutically acceptable salt thereof corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents such as nitrates, beta-adrenergic blocking agents, diuretics, hypotensive agents and the like can also be present.

Although the dosage and dosage regimen must in each case be carefully adjusted, utilizing sound professional judgment and considering the age, weight and condition of the recipient, the route of administration and the nature and gravity of the illness, generally the dosage will be from about 5 to about 300 mg per day, preferably from about 10 to about 100 per day of said compound or said salt thereof for an average adult. In some instances, a sufficient therapeutic effect can be obtained at a lower dose, while in others a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and, optionally, with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccarin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as for example myristyl palmitate, or mixtures thereof.

The pharmaceutical compositions according to the present invention are preferably administered orally, intra-hisalogically, parenterally, topically or rectally.

A further aspect of the present invention involves a method of effecting alpha- and beta-adrenergic blocking action and of treating hypertension in humans and animals which comprises adminstering to a human or animal in need thereof a therapeutically effective amount of a composition as above described.

The following non-limitative examples more particularly illustrate the present invention:

EXAMPLE 1

1-(3-Chloro-3-piperidinophenoxy)-3-(4-phenyl-1-piperazinyl)-2-propanol.

(a) A mixture of 7.47 grams of 2-chloro-3-piperidinophenol, 29.00 grams of epibromohydrin, 28.79 grams of potassium carbonate and 400 ml of acetonitrile is heated to reflux for twenty hours, insoluble matters are removed therefrom by filtration, the filtrate is entirely concentrated to dryness, and the residue is purified by a silica gel chromatography followed by recrystallization from n-hexane to give 8.0 grams (85%) of 1-(2-chloro-3-piperidinophenoxy)-2,3-epoxypropane as colorless crystals of m.p. 55°–57° C. NMR (CDCl$_3$): δ 1.55–1.95 (m, 6H), 2.75–3.19 (m, 7H), 4.10 (dd, 1H, J=11 Hz and 14 Hz), 4.18 (dd, 1H, J=11 Hz and 21 Hz), 6.54–6.77 (m, 2H). Elementary analysis calculated as C$_{14}$H$_{18}$ClNO$_2$: C 62.80, H 6.78, N 5.23, Cl 13.24; Found: C 62.61, H 6.87, N 5.08, Cl 13.15.

(b) 1-(2-Chloro-3-piperidinophenoxy)-2,3-epoxypropane (2.53 grams) obtained in (a) is heated to reflux for twelve hours with 4.60 grams of 1-phenylpiperazine and 200 ml of ethanol, the solvent is evaporated therefrom, the residue is purified by a silica gel chromatography, and recrystallized from ethanol to give 4.06 grams (86%) of the desired 1-(2-chloro-3-piperidinophenoxy)-3-(4-phenyl-1-piperazino)-2-propanol as colorless crystals of m.p. 107°–108° C. NMR (CDCl$_3$): δ 1.65–2.00 (m, 6H), 2.50–3.32 (m, 15H), 4.01–4.28 (m, 3H), 6.51–7.41 (m, 8H). Elementary analysis calculated as C$_{24}$H$_{32}$ClN$_3$O$_2$: C 67.04, H 7.56, N 9.77, Cl 8.25; Found: C 66.90, H 7.70, N 9.47, Cl 8.21.

(c) 1-(2-Chloro-3-piperidinophenoxy)-3-(4-phenyl-1-piperazino)-2-propanol obtained in (b) is converted to its maleate (monohydrogen) and recrystallized from a mixture of ethanol and ether to give desired monohydrogen-maleate as colorless crystals of m.p. 150°–152° C. NMR (d$_6$-DMSO): δ 1.51–1.80 (m, 6H), 2.80–3.15 (m, 4H), 3.20–3.51 (m, 10H), 4.01–4.20 (m, 2H), 4.21–4.51 (m, 1H), 6.10 (s, 2H), 6.65–7.45 (m, 8H). Elementary analysis calculated as C$_{17}$H$_{27}$ClN$_2$O$_3$·C$_4$H$_4$O$_2$·¼H$_2$O: C 61.08, H 6.68, N 7.63, Cl 6.44; Found: C 61.10, H 7.06, N 7.38, Cl 6.20.

The compounds of Example 2-37 are produced in an analagous procedure to that described in Example 1:

EXAMPLES 2-37

| Example No | R$^1$ | R$^2$ | R$^3$ | R$^4$ | Melting Point (°C.) | (Salt) |
|---|---|---|---|---|---|---|
| 2 | Me | —N⟨piperidine⟩ | H | H | 147~149 | M |
| 3 | Cl | " | H | H | 167~168 | M |
| 4 | Cl | " | Me | H | 166~167 | M |
| 5 | Cl | " | —CO$_2$Et | H | 165~166 | M |
| 6 | Cl | " | H | OEt / 4-CHMe | 116~118 | F |
| 7 | Cl | " | H | 2-OMe | 152~153 | M |
| 8 | Me | " | H | 2-OMe | 152~153 | M |
| 9 | Cl | " | H | 4-OMe | 180~181 | M |
| 10 | Cl | " | H | 3-Cl | 163~165 | M |
| 11 | Cl | " | H | 4-COMe | 158~159 | M |
| 12 | Me | —N⟨piperidone(=O)⟩ | H | H | 122~125 | F |
| 13 | Me | " | H | 2-OMe | 94~96 | F |
| 14 | H | —N⟨piperidine⟩ | H | H | 151~152 | M |
| 15 | Me | —N⟨piperidine⟩ | H | H | 159~161 | M |
| 16 | Br | " | H | H | 155~156 | M |
| 17 | Cl | " | Me | H | 167~168 | M |
| 18 | H | " | H | 2-Me | (glassy) | 3HCl |
| 19 | Me | " | H | 2-Me | 128~129 | M |
| 20 | Cl | " | H | 2-Me | 126~128 | M |
| 21 | H | " | H | 2-OMe | 117~120 | M |
| 22 | Me | " | H | 2-OMe | 136~138 | M |
| 23 | Cl | " | H | 2-OMe | 132~134 | M |
| 24 | Br | " | H | 2-OMe | 122~125 | M |
| 25 | Cl | " | H | 4-OMe | 145~147 | M |
| 26 | Br | " | H | 4-OMe | 134~135 | M |
| 27 | Me | " | H | 3-Cl | 99~101 | M |

-continued

| Example No | R¹ | R² | R³ | R⁴ | Melting Point (°C.) | (Salt) |
|---|---|---|---|---|---|---|
| 28 | Me | —N(piperidinone) | H | H | 105–111 | F |
| 29 | H | " | H | H | 102–106 | 2HCl |
| 30 | H | " | H | 2-Me | 145–147 | F |
| 31 | H | —N(piperidinone) | H | 2-Me | 129–131 | F |
| 32 | H | " | H | 2-OMe | 129–131 | M |
| 33 | Me | " | H | 2-OMe | 106–111 | F |
| 34 | Cl | —N(piperidine) | H | H | 124–125 | M |
| 35 | Cl | —N(morpholine) | H | H | 144–145 | M |
| 36 | Cl | " | H | Me | 144–146 | M |
| 37 | Cl | " | Me | H | 182–184 | M |

F: free compound
M: maleate

The phenolic compounds of the formula (II) which are used as starting material for compounds of the formula (I) may be prepared as follows:

Starting Material Production

2-Chloropiperidinophenol.

2-Chloro-3-piperidino-2-cyclohexenone (19.95 grams) and 9.19 grams of sodium acetate are dissolved in 500 ml of methanol and, with ice cooling and stirring, a solution of 17.25 grams of bromine in 200 ml of methanol is dropped thereinto during one hour. The mixture is stirred for another one hour at the same temperature, a solution of 26.2 grams of potassium hydroxide in 300 ml of methanol is dropped thereinto during 0.30 minutes, the mixture is stirred for one hour at room temperature, concentrated to about ¼ volume in vacuo, 400 ml of ice water is added thereto, then neutralized with 10% hydrochloric acid, separated matters therefrom are extracted with ether, the organic solvent layer is washed with saturated sodium chloride solution, dried with sodium sulfate, the solvent is evaporated therefrom, the residue is purified with silica gel chromatography, and recrystallized from n-hexane to give 14.71 grams (74.4%) of the product as colorless crystals of m.p. 91.5°–92.0° C.

Starting from the corresponding (II), the following intermediates (III) are prepared.

1-(2-Chloro-5-methyl-3-(1-pyrrolidinyl)-phenoxy)-2,3-epoxypropane. Oily substance. Mass spectra: $M^+ = 2.67$. NMR (CDCl$_3$): δ 1.80–2.20 (m, 4H), 2.27 (s, 3H), 2.81 (s, 1H), 2.87 (d, 1H, J=3 Hz), 3.10–3.52 (m, 5H), 4.00 (dd, 1H, J=4 Hz and 11 Hz), 4.28 (dd, 1H, J=3.5 Hz and 11 Hz), 6.20–6.50 (m, 2H).

1-(2-Chloro-5-methyl-3-piperidinophenoxy)-2,3-epoxypropane. Oily substance. NMR (CDCl$_3$): δ 1.30–2.10 (m, 6H), 2.26 (s, 3H), 2.78–3.15 (m, 6H), 3.16–3.50 (m, 1H), 3.95 (dd, 1H, J=5 Hz and 12 Hz), 4.25 (dd, 1H, J=4 Hz and 12 Hz), 6.45 (s, 2H).

1-(2-Chloro-3-(1-piperidinyl)-phenoxy)-2,3-epoxypropane. Oily substance. Mass spectra: $M^+ = 253$. NMR (CDCl$_3$): δ 1.80–2.15 (m, 4H), 2.67–2.93 (m, 2H), 3.20–3.55 (m, 5H), 3.71–4.40 (m, 3H), 6.35–6.65 (m, 2H), 7.02 (t, 1H, J=7.5 Hz).

1-(2-Chloro-5-ethoxycarbonyl-3-(1-pyrrolidinyl)-phenoxy)-2,3-epoxypropane. Oily substance (colorless). Mass spectra $M^+ = 325$. NMR (CDCl$_3$): δ 1.40 (t, 3H, J=7 Hz), 1.80–2.15 (m, 4H), 2.81 (s, 1H), 2.87 (d, 1H, J=2 Hz), 3.22–3.60 (m, 5H), 3.80–4.50 (m, 4H), 7.10 (d, 1H, J=1.5 Hz), 7.21 (d, 1H, J=1.5 Hz).

The alpha and beta-adrenergic blocking action and antihypertensive action of the compounds of the present invention and their pharmaceutically acceptable salts is illustrated by the representative data set forth below:

Alpha-Adrenergic Blocking Action

Test method is as follows. Thus, test compounds are given per os to ddY strain male mice (20 to 30 grams body weight; one group comprising five mice), then lethal dose of norepinephrine is injected to tail vein of the mice and, out of the survival numbers of the animals, the alpha-adrenergic blocking action of the test compounds is determined. In the Table 1, the doses where at least three mice out of five survived are given.

TABLE 1

| Compounds (Example Number) | Doses (mg/kg) |
|---|---|
| 1 | 1.0 |
| 3 | 10 |
| 7 | 2.5 |
| 12 | 1.0 |
| 13 | 1.0 |
| 16 | 1.0 |
| 17 | 10 |
| 22 | 5 |
| 23 | 1.0 |
| 24 | 1.0 |
| 27 | 1.0 |
| 28 | 2.5 |
| 29 | 2.5 |
| 33 | 2.5 |
| 35 | 2.5 |
| Prazosin | 10 |

Beta-Adrenergic Blocking Action

Test compounds were administered orally to unanesthetized male rats (250–350 grams body weight; 5 rats in each group) and, one hour thereafter, isoproterenol (0.01 mg/kg) was injected intravenously and the heart rate increase induced thereby was measured. This was compared with the control and the effect of inhibiting the increase by each test compound was calculated wherefrom the beta-adrenergic blocking action of the test compounds was evaluated. Table 2 below shows the dose of test compound which inhibits at least 50% of the heart rate increase induced by isoprotereonol.

TABLE 2

| Compounds (Example Numbers) | Doses (mg/kg) |
| --- | --- |
| 1 | 25 |
| 35 | 50 |
| 7 | 50 |
| 22 | 25 |
| 13 | 25 |
| Propranolol | 2.5 |

Hypotensive Action on Oral Administration

Unanesthetized normal male rats (250 to 350 grams body weight; one group comprising 5 to 6 rats) are used and changes in blood pressure by oral administration of test compounds are observed by indirectly tail cuff method. The results are given in Table 2. Blood pressure change rate (%) is calculated by the following expression:

Blood pressure change rate (%) =

$$\frac{\text{Blood pressure (mmHg) after Administration}}{\text{Blood pressure (mmHg) before Administration}} \times 100$$

TABLE 3

| Compounds (Example Number) | Doses (mg/kg) | Blood Pressure Change Rate (%) min after administration | | | |
| --- | --- | --- | --- | --- | --- |
| | | 0 | 120 | 240 | 350 |
| 1 | 50 | 100 | 86.2 | 78.1 | 70.4 |
| | 5 | 100 | 88.1 | 80.1 | 79.3 |
| 3 | 50 | 100 | 87.2 | 84.5 | 82.0 |

The compound of Example 13 is representative of the present invention compounds. The hypotensive action and heart rate changes resulting from administration of that compound to natural hypertensive rats and its effects on urine volume and electrolytes in urine in renally hypertensive rats is shown below.

Natural hypertensive rats showing not less than 180 mmHg systolic pressure are used. Under unanesthetized condition, a bloodless blood pressure measuring apparatus is used and the pressure is observed at tail artery. Thus, blood pressures and heart rates are measured with definite time intervals during the course of before and after administration of the compound. The results are given in Table 4.

TABLE 4

| Hours after Administration | 0.1 mg/kg by oral route | | 1.0 mg/kg by oral route | |
| --- | --- | --- | --- | --- |
| | Systolic Pressure (mmHg) | Heart Rate (beats/min) | Systolic Pressure (mmHg) | Heart Rate (beats/min) |
| 0 | 191.3 ± 3.0 | 504 ± 10 | 190.2 ± 3.0 | 498 ± 13 |
| 1 | 178.0 ± 6.7 | 512 ± 3 | 168.0 ± 6.1 | 511 ± 14 |
| 3 | 168.7 ± 3.0 | 519 ± 10 | 161.8 ± 5.2 | 486 ± 18 |
| 6 | 165.3 ± 4.7 | 499 ± 14 | 157.4 ± 8.0 | 498 ± 15 |
| 9 | 172.3 ± 7.8 | 510 ± 8 | 174.6 ± 9.1 | 507 ± 3 |
| 12 | 180.5 ± 8.3 | 486 ± 14 | 170.8 ± 3.3 | 492 ± 9 |
| 24 | 189.7 ± 7.8 | 496 ± 18 | 189.0 ± 3.0 | 507 ± 13 |

(Figures in the table are mean value ± standard deviation)

Effects on Urine Volume and Electrolytes in Urine of Renally Hypertensive Rats.

Five renally hypertensive rats are made one group. Test compound is given orally and, simultaneously, 20 ml/kg of physiological saline solution (0.9% NaCl) is given orally. Effects of the test compound on urine volume and on electrolytes in urine are measured until 24 hours after administration. The results are given in Table 5.

TABLE 5

| Compounds (Example Numbers) | Doses (mg/kg) per os | Urine Volume (ml) | Electrolytes | | |
| --- | --- | --- | --- | --- | --- |
| | | | Na+ (mEq) | K+ (mEq) | Na+/K+ |
| Results for the first 12 Hours: | | | | | |
| Control | 0 | 11.7 ± 1.5 | 1.58 ± 0.19 | 0.41 ± 0.07 | 4.55 ± 0.66 |
| 13 | 0.1 | 13.6 ± 1.3 | 1.13 ± 0.13 | 0.23 ± 0.03 | 5.68 ± 0.93 |
| Prazosin | 0.125 | 8.0 ± 0.7 | 0.74 ± 0.08 | 0.38 ± 0.04 | 2.18 ± 0.30 |
| Results for the first 24 Hours: | | | | | |
| Control | 0 | 14.5 ± 1.7 | 1.97 ± 0.18 | 0.58 ± 0.18 | 3.90 ± 0.52 |
| 13 | 0.1 | 19.0 ± 2.6 | 0.36 ± 0.04 | 1.65 ± 0.22 | 5.23 ± 0.88 |
| Prazosin | 0.125 | 12.1 ± 1.0 | 0.62 ± 0.05 | 1.31 ± 0.11 | 2.23 ± 0.22 |

(Figures in the table are mean value ± standard deviation)

What is claimed is:

1. A compound of the formula (I):

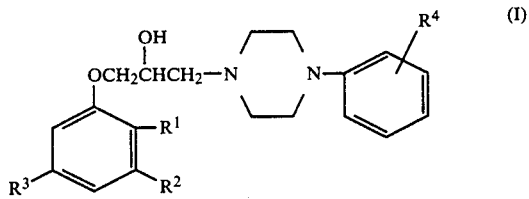

or a pharmaceutically acceptable salt thereof wherein $R^1$ is hydrogen, halo or lower alkyl; $R^2$ is

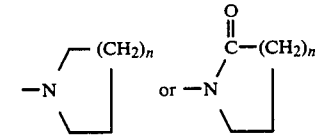

where n is 1, 2 or 3; $R^3$ is hydrogen, lower alkyl or lower alkoxycarbonyl; and $R^4$ is hydrogen, lower alkyl unsubstituted or alpha-substituted by lower alkoxy, lower alkoxy, halo or lower alkanoyl.

2. A compound according to claim 1 wherein $R^1$ is hydrogen, fluoro, chloro, bromo or alkyl of 1 to 4 carbon atoms.

3. A compound according to claim 1 wherein $R^3$ is hydrogen, alkyl of 1 to 4 carbon atoms or alkoxycarbonyl of 1 to 4 carbon atoms in the alkoxy moiety.

4. A compound according to claim 1 wherein $R^4$ is hydrogen, alkyl of 1 to 4 carbon atoms unsubstituted or substituted by alkoxy of 1 to 4 carbon atoms, alkoxy of 1 to 4 carbon atoms, fluoro, chloro, bromo or alkanoyl of 1 to 4 carbon atoms in the alkyl portion.

5. A compound according to claim 1 in the form of a pharmaceutically acceptable salt.

6. A pharmaceutical composition useful for effecting both alpha-adrenergic blocking action and beta-adrenergic blocking action and for treating hypertension in humans and animals which comprises a therapeutically effective amount of a compound of the formula (I):

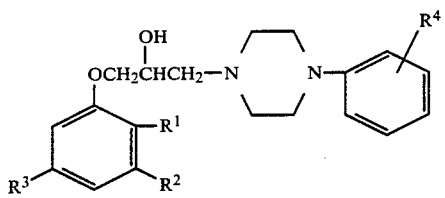

or a pharmaceutically acceptable salt thereof wherein $R^1$ is hydrogen, halo or lower alkyl; $R^2$ is

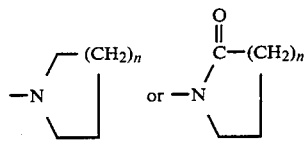

where n is 1, 2 or 3; $R^3$ is hydrogen, lower alkyl or lower alkoxycarbonyl; and $R^4$ is hydrogen, lower alkyl unsubstituted or alpha-substituted by lower alkoxy, lower alkoxy, halo or lower alkanoyl, in combination with a pharmaceutically acceptable carrier.

7. A composition according to claim 6 wherein $R^1$ is hydrogen, fluoro, chloro, bromo or alkyl of 1 to 4 carbon atoms.

8. A composition according to claim 6 wherein $R^3$ is hydrogen, alkyl of 1 to 4 carbon atoms or alkoxycarbonyl of 1 to 4 carbon atoms in the alkoxy moiety.

9. A composition according to claim 6 wherein $R^4$ is hydrogen, alkyl of 1 to 4 carbon atoms unsubstituted or substituted by alkoxy of 1 to 4 carbon atoms, alkoxy of 1 to 4 carbon atoms, fluoro, chloro, bromo or alkanoyl of 1 to 4 carbon atoms in the alkyl portion.

10. A composition according to claim 6 wherein the compound is in the form of a pharmaceutically acceptable salt.

11. A method of effecting both alpha-adrenergic blocking action and beta-adrenergic blocking action and treating hypertension in humans and animals which comprises administering to a human or animal in need thereof a therapeutically effective amount of a compound of the formula (I):

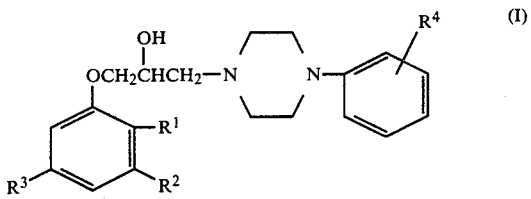

or a pharmaceutically acceptable salt thereof wherein $R^1$ is hydrogen, halo or lower alkyl; $R^2$ is

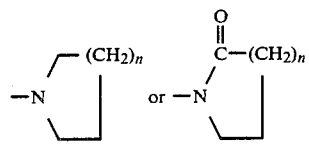

where n is 1, 2 or 3; $R^3$ is hydrogen, lower alkyl or lower alkoxycarbonyl; and $R^4$ is hydrogen, lower alkyl unsubstituted or alpha-substituted by lower alkoxy, lower alkoxy, halo or lower alkanoyl, in combination with a pharmaceutically acceptable carrier.

12. A method according to claim 11 wherein $R^1$ is hydrogen, fluoro, chloro, bromo or alkyl of 1 to 4 carbon atoms.

13. A method according to claim 11 wherein $R^3$ is hydrogen, alkyl of 1 to 4 carbon atoms or alkoxycarbonyl of 1 to 4 carbon atoms in the alkoxy moiety.

14. A method according to claim 11 wherein $R^4$ is hydrogen, alkyl of 1 to 4 carbon atoms unsubstituted or substituted by alkoxy of 1 to 4 carbon atoms, alkoxy of 1 to 4 carbon atoms, fluoro, chloro, bromo or alkanoyl of 1 to 4 carbon atoms in the alkyl portion.

15. A method according to claim 11 wherein the compound is in the form of a pharmaceutically acceptable salt.

* * * * *